United States Patent [19]

Shaw et al.

[11] Patent Number: 4,963,333

[45] Date of Patent: Oct. 16, 1990

[54] UNIVERSAL EVAPORATION COVER

[75] Inventors: James D. Shaw; Martin F. Muszak, Rochester, both of N.Y.

[73] Assignee: Eastman Kodak Company, Rochester, N.Y.

[21] Appl. No.: 346,205

[22] Filed: May 2, 1989

[51] Int. Cl.$^5$ ............................................. B01L 3/00
[52] U.S. Cl. ....................................... 422/99; 422/63;
422/65; 422/104; 350/534
[58] Field of Search ...................... 422/99, 63, 65, 104;
350/534

[56] References Cited

U.S. PATENT DOCUMENTS

| | | | |
|---|---|---|---|
| 4,298,571 | 11/1981 | DiFulvio et al. | 422/65 |
| 4,584,275 | 4/1986 | Okano et al. | 422/63 X |
| 4,814,279 | 3/1989 | Sugaya | 422/104 X |

FOREIGN PATENT DOCUMENTS 0191650 8/1986 European Pat. Off. ............. 422/99

*Primary Examiner*—Robert J. Warden
*Assistant Examiner*—Lynn Kummert
*Attorney, Agent, or Firm*—Dana M. Schmidt

[57] ABSTRACT

There is disclosed an evaporation cover that is useful to cover two types of test elements having different sample wetting locations, namely potentiometric types and colorimetric types. Both are accommodated by constructing enough of the flat sealing portion of the undersurface so as to sealingly cover the wetted area of the colorimetric type, and by providing on the cover, means for camming the cover away from a test element that is being loaded under the cover.

4 Claims, 3 Drawing Sheets

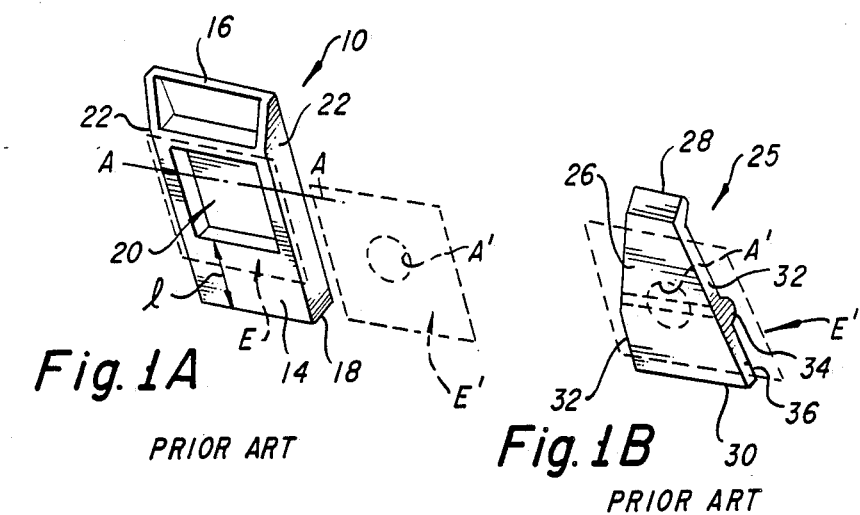
Fig. 1A PRIOR ART
Fig. 1B PRIOR ART
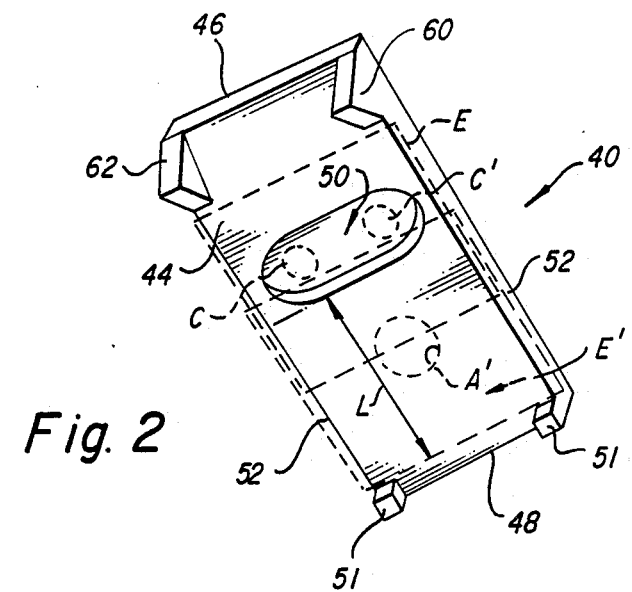
Fig. 2

UNIVERSAL EVAPORATION COVER

FIELD OF THE INVENTION

The invention concerns evaporation covers used in analyzer incubators, and specifically a cover that must be useful with either a colorimetric type test element, or a potentiometric type.

BACKGROUND OF THE INVENTION

Conventional blood analyzers have provided separate incubators for separate functions—the test elements that provide a potentiometric assay are incubated separately from those that provide a colorimetric assay. However, there has been a need to combine features and to simplify, whereby a single incubator can be used to incubate both colorimetric and potentiometric test elements. In such a case, each station of the incubator has to be capable of receiving either type of test element.

Such a single incubator construction has had the problem, prior to this invention, of not having an evaporation cover that could be used for either test element. Instead, the cover used on the colorimetric incubator was useful only for the colorimetric test element, and similarly the cover in the potentiometric incubator was useful only for the potentiometric test element. The reason was that the cover is intended to seal off from evaporation, the areas of the test element wetted by the sample. In commonly used test elements such as those sold under the trademark "Ektachem" by Eastman Kodak, the wetted areas occupy different parts of the test element geometry. Furthermore, a recess is formed in the cover for the potentiometric elements, in light of the fact that liquid tends to protrude from such an element. However, no such liquid protrudes from the colorimetric element, and instead the cover needs to seal flush against the latter, to insure a minimum evaporation loss. Such a flush, sealing fit is not appropriate for a potentiometric test element, and indeed tends to cause contact with the sample drop on the test element, thus contaminating that station of the incubator.

Camming means have been provided in some analyzers to raise the cover as a test element, such as a potentiometric element, is loaded, as shown, for example, in FIG. 4 of U.S. Pat. No. 4,298,571. However, such a construction requires the analyzer to have a separate, active element for camming the cover away, instead of providing for such means on the cover itself.

Thus, prior to this invention it has not been possible to provide a single incubator for both types of test elements, because there has been available no evaporation cap that would be effective for both types.

SUMMARY OF THE INVENTION

We have constructed an evaporation cover for an incubator that is useful for both types of test elements.

More specifically, there is provided an evaporation cover for an incubator that receives test elements, the cover including a body portion of sufficient length to cover at least a portion of a test element in the incubator, the body portion having (a) a recess to provide clearance for liquid drops sitting on a potentiometric test element, (b) a front edge, (c) a rear edge, and (d) two side edges; the length of the body portion extending generally parallel to the side edges; the improvement wherein the body portion length is extended beyond the recess towards the rear edge, by an amount that is sufficient to allow a colorimetric element to be pushed beyond the recess and still have its wetted area be sealingly covered, and further including means on the body portion for camming the body portion away from a test element that is entering the incubator.

Accordingly, it is an advantageous feature of the invention that test elements of both potentiometric and colorimetric types can be incubated in one incubator, because an evaporation cover is now available that is useful with both.

Other advantageous features will become apparent upon reference to the following detailed description of the invention, when read in light of the attached drawings.

BRIEF DESCRIPTION OF THE DRAWINGS

FIG. 1A and 1B are bottom perspective views of the underside of evaporation covers of the prior art, the phantom lines being representative of test elements that would fit under those covers;

FIG. 2 is a perspective view similar to that of FIG. 1, but illustrating the cover of the invention;

DESCRIPTION OF THE PREFERRED EMBODIMENTS

Figure 3:
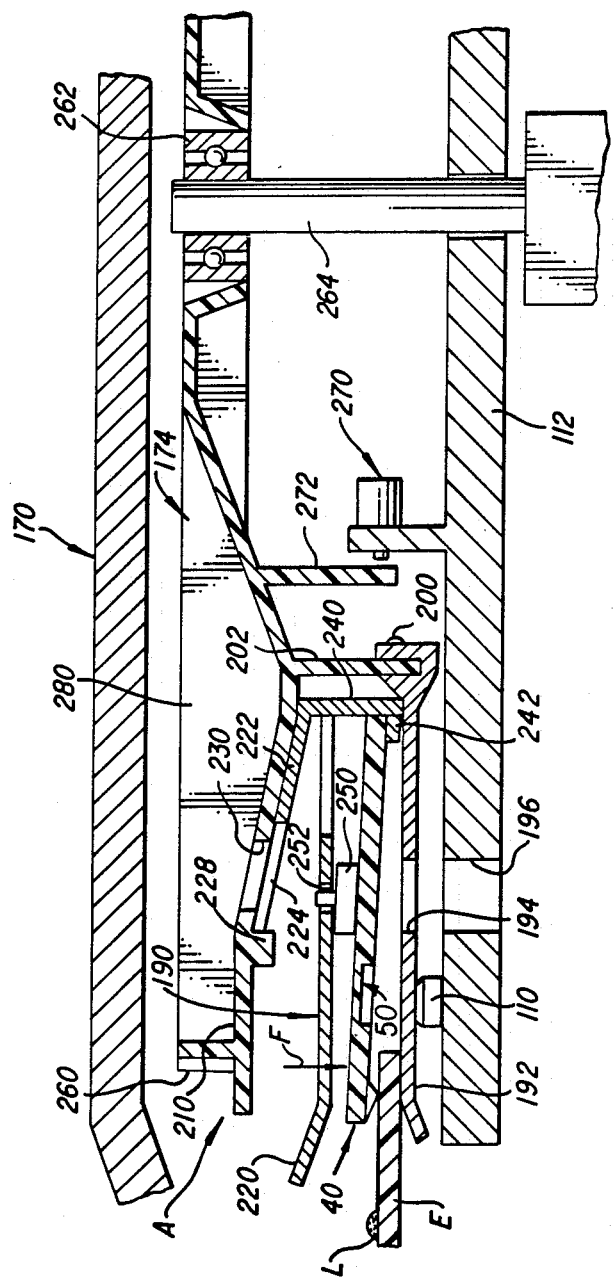
FIG. 3 is a fragmentary side elevational view in section, illustrating the mounting of the cover of FIG. 2 in an incubator and the introduction of a test element.

The cover of this invention is described in connection with certain preferred dried, slide-like test elements and a preferred incubator construction, for example, colorimetric test elements of the type described in U.S. Pat. No. 3,992,158 and potentiometric test elements of the type described in U.S. Pat. No. 4,053,381. In addition, it is useful wherever both a colorimetric and a potentiometric element are to be covered at separate times in the same station, regardless of the type of incubator construction or individualized test element construction.

As noted above, the wetting area of the potentiometric elements involves protruding liquid, usually, so that the cover preferably provides a recess aligned with this area to keep the cover from contacting the liquid. Thus, as shown in FIG. 1A, a cover 10 of the prior art has a body portion having an undersurface 14, a front edge 16, a back edge 18, and a recess 20 between those two edges. Side surfaces 22 extend between the front and back edges. Recess 20 is designed to encompass the wetted area of a potentiometric test element E, shown in phantom, such wetted area being located generally on line A—A, which is not centered on the element.

In contrast, the wetted area A' of a colorimetric test element E', shown in phantom and displaced to one side, FIG. 1A, is centered in the element, and lacks liquid protruding above its surface. Accordingly, undersurface 26 of conventional cover 25, FIG. 1B, fits flush against the element E' to sealingly cover wetted area A'. As used herein "sealingly cover" means, a flush contact between the upper surface of the test element and the undersurface of the cover at the area in question. Cover 25 also has a front edge 28, back edge 30, and side surfaces 32, but no recess portion in undersurface 26. (Rib 34 on the top surface 36 has no effect on the flush fit of undersurface 26 against element E'.)

The colorimetric element E' in FIG. 1A is positioned alongside where it would be if it were substituted for element E and pushed all the way back so that its back edge is flush with cover back edge 18. Because distance "l" between edge 18 and recess 20 is so short, such an arrangement would not sealingly cover wetted area A', since that area would be uncovered due to the recess 20.

A further disadvantage of prior art cover 10, FIG. 1A, is that undersurface 14 cannot clear the surface of a potentiometric element E being loaded under it. Instead, a separate plunger (not shown) has to be used to push cover 10 away during such loading.

In accordance with the invention, cover 40, FIG. 2, is constructed to be universally useful, that is, with both a colorimetric test element and a potentiometric test element. Thus, it comprises a body portion having an undersurface 44, a front edge 46, a back edge 48, and a recess 50 between the edges. Two feet 51 extend from undersurface 44 adjacent edge 48. Side surfaces 52 extend between the front and back edges. Recess 50, like recess 20 in prior art cover 10, encompasses the wetted area of a potentiometric test element E, shown in phantom with two circles C, $C^1$ representing the two protruding drops of liquid on such an element. However, unlike prior art cover 10, undersurface 44 has a length L extending from recess 50 back towards rear edge 48, that will accommodate and sealingly cover all of the exposed wetted area A' of a colorimetric element E' that is positioned rearwardly so that its back edge b' is aligned with feet 51. This is apparent in FIG. 4B, where dimension "w", the width of the viewing aperture 194, corresponds generally to the width of the wetted area A'.

An additional feature of the cover of this invention is the provision of means on the cover for camming the cover away from a test element during the loading operation. Preferably, such means comprise two projections, such as feet 60, 62 that extend out away from undersurface 44 along each of the side surfaces 52, adjacent front edge 46. As shown in FIG. 3, they are shaped so that during the loading of an element E (or E'), the cover raises up away from the element so that any drop of liquid L that might protrude, does not wipe itself on cover 40. However, FIG. 4A, once the loading operation is complete, feet 60 and 62 drop off the front edge F of element E, and recess 50 accommodates the drop L.

Feet 51, 60 and 62 provide an additional function—after a test element is removed from the incubator, air can pass under cover 40 and clear out any residual gases that might be left from the element that was there.

Preferably, surface 44 of the cover is a non porous material, such as polyethylene.

Cover 40 is related to the structure of an incubator 170 preferably as is shown in FIG. 3. A rotor 174 is journaled at 262 on a shaft 264, and has a plurality of stations formed in the rotor, station A being depicted. A spring 190 is captured at the station and is biased to press down on the cover with a force F. Such a spring comprises a cover—engaging leg 220, a bias leg 222, and a vertical leg 240, leg 222 being captured behind ridge 228 of rotor 174. A boss 250 can be mounted on the top of cover 40 to releasably engage an aperture 252 in leg 220. Vertical leg 240 rests on a support plate 192 that is apertured at 194 for the reading of colorimetric test elements. Plate 192 is also the support of the test element E and E', FIGS. 4A and 4B. The undersurface of plates 192 are caused to ride over buttons 110, in stationary surface 112, positioned to carefully control the height of the test element vis-a-vis a photodetector, not shown, positioned to read a colorimetric test element through apertures 194 and 196. Sensor 270 and flag 272 can be used to accurately sense when the stations are in their correct positions, e.g., for reading.

Figure 4A:
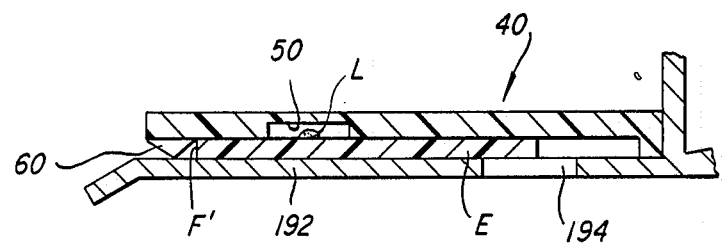
FIG. 4A and 4B are fragmentary views similar to a portion of the view in FIG. 3, showing either type of test element in place in the incubator.
Figure 4B:
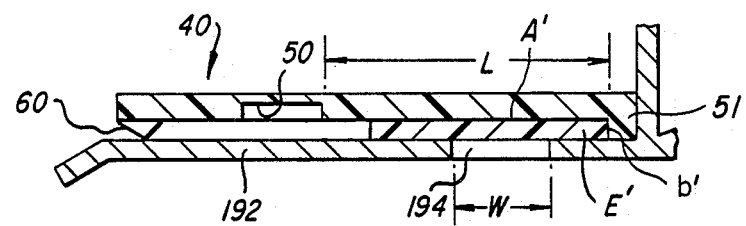

A pusher blade (not shown), of any suitable construction, is used to push a potentiometric test element E, FIG. 4A, into the partially advanced position shown under cover 40, where it remains for incubation, and a colorimetric test element E', into the fully advanced position shown in FIG. 4B, where it remains for incubation and for reading. (Potentiometric elements are preferably read by removing them from the incubator.)

Regardless of the type of test element present, such elements are removed from incubator station A by a conventional blade, not shown.

The invention has been described in detail with particular reference to preferred embodiments thereof, but it will be understood that variations and modifications can be effected within the spirit and scope of the invention.

What is claimed is:

1. In an evaporation cover for an incubator that receives both colorimetric and potentiometric test elements, the cover including a body portion of sufficient length to cover at least a portion of a test element in the incubator, said body portion having (a) a sealing surface to contact a test element, (b) a recess in said sealing surface to provide clearance for liquid drops sitting on a potentiometric test element, (c) a front edge, (d) a rear edge and (e) two side edges; said body portion length extending generally parallel to said side edges; the improvement wherein said body portion length is extended beyond said recess towards said rear edge, by an amount that is sufficient to allow a colorimetric element to be pushed beyond said recess and still have its wetted area be sealingly covered, and further including means on said body portion for camming said body portion away from a test element that is entering said incubator.

2. A cover as defined in claim 1, wherein said camming means comprise a projection extending away from body portion along each of said side edges and adjacent said front edge, shaped to ride over a test element inserted under the cover until such element is fully inserted.

3. In an evaporation cover for an incubator that receives both colorimetric and potentiometric test elements that have an area that is wetted by patient sample, the cover including a body portion having a front edge and a back edge spaced the length of the cover from said front edge, an undersurface between said edges that contacts a received test element, a recess in said undersurface between said edges to provide space for protruding liquid, and two outside edge surfaces connecting said front and back edges;

the improvement wherein the space of said undersurface between said recess and said back edge is lengthened to accommodate all of the wetted area of a colorimetric test element within said space, and further including means on said body portion for camming said body portion away from a test element that is entering said incubator.

4. A cover as defined in claim 3, wherein said camming means comprise a projection extending away from body portion along each of said side edges and adjacent said front edge, shaped to ride over a test element loaded under the cover until such element is fully loaded.

* * * * *

UNITED STATES PATENT AND TRADEMARK OFFICE
CERTIFICATE OF CORRECTION

PATENT NO. : 4,963,333

DATED : October 16, 1990

INVENTOR(S) : James D. Shaw & Martin F. Muszak

It is certified that error appears in the above-identified patent and that said Letters Patent is hereby corrected as shown below:

Column 3, line 44 should read --F' of element E, and recess 50 accommodates the drop--.

Column 4 line 15 should read --elements are removed from incubator station A by--.

Column 4, line 16 should read --conventional picker fingers, not shown.--.

Signed and Sealed this

Thirty-first Day of March, 1992

Attest:

HARRY F. MANBECK, JR.

*Attesting Officer*           *Commissioner of Patents and Trademarks*